(12) United States Patent
Belford et al.

(10) Patent No.: US 7,851,745 B2
(45) Date of Patent: Dec. 14, 2010

(54) FLAT PLATE FAIMS WITH LATERAL ION FOCUSING

(75) Inventors: Michael W. Belford, Los Altos, CA (US); Viatcheslav V. Kovtoun, Santa Clara, CA (US)

(73) Assignee: Thermo Finnigan LLC, San Jose, CA (US)

( * ) Notice: Subject to any disclaimer, the term of this patent is extended or adjusted under 35 U.S.C. 154(b) by 236 days.

(21) Appl. No.: 12/334,313

(22) Filed: Dec. 12, 2008

(65) Prior Publication Data

US 2010/0148053 A1    Jun. 17, 2010

(51) Int. Cl.
*H01J 49/40* (2006.01)

(52) U.S. Cl. .................. 250/286; 250/287; 250/281; 250/282

(58) Field of Classification Search .......... 250/286, 250/287, 281, 282
See application file for complete search history.

(56) References Cited

U.S. PATENT DOCUMENTS

| 6,495,823 | B1 | | 12/2002 | Miller et al. | |
|---|---|---|---|---|---|
| 7,399,959 | B2 | * | 7/2008 | Miller et al. | 250/287 |
| 7,550,717 | B1 | * | 6/2009 | Belford et al. | 250/281 |
| 2003/0057367 | A1 | | 3/2003 | Guevremont et al. | |
| 2004/0135080 | A1 | | 7/2004 | Ouyang et al. | |
| 2009/0206250 | A1 | * | 8/2009 | Wollnik | 250/290 |

FOREIGN PATENT DOCUMENTS

| WO | WO 01/69216 A2 | 9/2001 |
|---|---|---|
| WO | WO 2007/136373 A1 | 11/2007 |
| WO | WO 2008/067331 A2 | 6/2008 |

* cited by examiner

*Primary Examiner*—Kiet T Nguyen
(74) *Attorney, Agent, or Firm*—Freedman & Associates; Charles B. Katz (57) ABSTRACT

A high field asymmetric waveform ion mobility spectrometer (FAIMS) includes at least two focusing electrodes that are separated one from the other by a gap, which decreases in width along a direction of ion flow. Within the gap is disposed an electrode assembly including a first electrode and a second electrode, approximately flat surfaces of the first and second electrodes facing one another so as to define a space of approximately uniform thicknesses therebetween. During use electrical signals are applied via an electrical contact on at least one of the first electrode and the second electrode, and on each one of the at least two focusing electrodes. The electrical signals are for establishing electrode electric field conditions within the space between the first electrode and the second, for selectively transmitting ions therethrough and for directing the selectively transmitted ions in a direction away from one of the at least two focusing electrodes and toward a central portion of the space.

22 Claims, 8 Drawing Sheets

FLAT PLATE FAIMS WITH LATERAL ION FOCUSING

FIELD OF THE INVENTION

The instant invention relates generally to High Field Asymmetric Waveform Ion Mobility Spectrometry (FAIMS), and more particularly to FAIMS with a flat-plate electrode geometry supporting laterally directed ion focusing.

BACKGROUND OF THE INVENTION

High Field Asymmetric Waveform Ion Mobility Spectrometry (FAIMS) is a technology that is capable of separating gas-phase ions at atmospheric pressure. Ions are introduced into an analyzer region, across which is applied a radio frequency (rf) waveform, such that the ions are subjected to alternating high and low strength electric fields. The applied waveform is asymmetric, comprising a repeating pattern including a high voltage component, $V_1$, lasting for a short period of time $t_2$ and a lower voltage component, $V_2$, of opposite polarity, lasting a longer period of time $t_1$. In particular, the waveform is synthesized such that the integrated voltage-time product, and thus the field-time product, during each complete cycle of the waveform is zero, for instance $V_1 t_2 + V_2 t_1 = 0$; for example +2000 V for 10 µs followed by −1000 V for 20 µs. The peak voltage, $V_1$, during the shorter duration, high voltage portion of the waveform is called the "dispersion voltage" or DV.

Ions are separated in FAIMS on the basis of a difference in the mobility of an ion at high field strength, $K_h$, relative to the mobility of the ion at low field strength, K. In other words, the ions are separated because of the compound dependent behavior of $K_h$ as a function of the applied electric field strength. This field-dependent change in the mobility of the ions causes the ions to drift toward the walls of the analyzer region. In order to transmit an ion of interest through FAIMS, an appropriate direct current compensation voltage (CV) is applied to compensate for the drift of the ion of interest toward the analyzer walls. By varying the compensation voltage, different ions are selectively transmitted through the FAIMS device.

In general, the electrodes that define the analyzer region in a FAIMS device may be either flat or curved in shape, such as for instance parallel flat-plate electrodes or concentric-cylinder electrodes, respectively. The concentric-cylinder configuration provides higher sensitivity compared to the flat-plate configuration. This higher sensitivity is due to a two-dimensional atmospheric pressure ion-focusing effect that occurs in the analyzer region between the curved electrode surfaces of the concentric-cylinder electrodes. When no electrical voltages are applied to the cylinders the radial distribution of ions should be approximately uniform across the FAIMS analyzer. During application of DV and CV, however, the radial distribution of ions is not uniform across the annular space of the FAIMS analyzer region. With the application of an appropriate DV and CV for an ion of interest, those ions become focused into a band between the electrodes and the rate of loss of ions, as a result of collisions with the FAIMS electrodes, is reduced. The efficiency of transmission of the ions of interest through the analyzer region of a concentric-cylinder FAIMS is thereby improved as a result of this two-dimensional ion focusing effect.

On the other hand, the parallel flat-plate electrode configuration provides higher resolution. Resolution of a FAIMS device is defined in terms of the extent to which ions having similar mobility properties are separated under a set of predetermined operating conditions. Thus, a high-resolution FAIMS device transmits selectively a relatively small range of ion types having similar mobility properties, whereas a low-resolution FAIMS device transmits selectively a relatively large range of ion types having similar mobility properties. The resolution of FAIMS in the concentric-cylinder configuration is compromised relative to the resolution in the parallel flat-plate configuration because the concentric-cylinder configuration has the capability of focusing and trapping ions, as described above. This focusing action means that ions of a wider range of mobility characteristics are simultaneously focused in the analyzer region between the concentric cylinder-electrodes. Furthermore, a concentric-cylinder FAIMS device with narrow electrodes has the strongest focusing action, but the lowest resolution for separation of ions. As the radii of curvature of the cylinders are increased, the focusing action becomes weaker, and the ability of FAIMS to simultaneously focus ions of similar high-field mobility characteristics is similarly decreased. This means that the resolution of FAIMS increases as the radii of the electrodes are increased, with the parallel flat-plate configuration having the maximum attainable resolution.

Unfortunately, the sensitivity of a parallel flat-plate FAIMS device is low compared to the concentric-cylinder design. This is because as the ions transit through the analyzer region between the parallel flat-plates, diffusion and ion-ion repulsion forces, even though they are small, cause the ions to spread out in a direction along the width of the plates. In other words, the ions are introduced into the space between the flat-plate electrodes as an approximately collimated beam of ions, but rapidly spread out toward the edges of the electrodes to form a sheet of ions that travels through the analytical gap to the ion outlet. Accordingly, there has always been a trade-off to be made in the prior art between sensitivity and resolution when selecting an electrode configuration for a FAIMS device.

It would be desirable to provide an apparatus and method that overcome at least some of the above-mentioned limitations.

SUMMARY OF EMBODIMENTS OF THE INVENTION

According to an aspect of the invention there is provided a high field asymmetric waveform ion mobility spectrometer (FAIMS), comprising: a first electrode having two non-parallel edges defining therebetween a width that decreases along a length of the first electrode, the first electrode having an approximately flat first electrode surface bounded by the two edges; a second electrode having two non-parallel edges defining therebetween a width that decreases along a length of the second electrode, the second electrode having an approximately flat second electrode surface bounded by the two edges, the second electrode disposed in a spaced-apart facing relationship with the first electrode so as to define an electrode assembly with a space of approximately uniform thicknesses between the first electrode surface and the second electrode surface, the two edges of the first electrode and the two edges of the second electrode cooperating to define two lateral boundaries of the electrode assembly with separation therebetween decreasing along a first direction, the space for supporting during use the transmission of ions through the electrode assembly along the first direction; at least two focusing electrodes including at least one focusing electrode disposed adjacent to each of the two lateral boundaries of the electrode assembly, the separation distance between the at least two focusing electrodes decreasing along the first direction; an electrical contact on at least one of the first electrode and the second electrode for receiving an asymmetric waveform potential and for applying a direct current compensation potential between the first electrode and the second electrode, for establishing an electric field within the space for separating ions according to the FAIMS principle; and, an electrical contact on each one of the at least two focusing electrodes for receiving a direct current electrical potential for directing ions in a direction away from one of the two lateral boundaries and toward a central portion of the space.

According to an aspect of the invention there is provided a high field asymmetric waveform ion mobility spectrometer (FAIMS), comprising: at least two focusing electrodes that are separated one from the other by a gap that decreases in width along a first direction; and, an electrode assembly disposed within the gap between the at least two focusing electrodes, the electrode assembly comprising: a first electrode having a first side that is bounded by an isosceles trapezoid-shaped perimeter, the first side being approximately flat; and, a second electrode having a second side that is bounded by an approximately same isosceles trapezoid-shaped perimeter, the second side being approximately flat, the second electrode disposed in a spaced-apart facing relationship with the first electrode so as to define between the first side and the second side a space of approximately uniform thickness, the space for supporting during use the transmission of ions through the electrode assembly along the first direction; wherein the decreasing width of the gap between the at least two focusing electrodes conforms approximately to the isosceles trapezoid-shaped perimeter of the first and second electrodes.

According to an aspect of the invention there is provided a high field asymmetric waveform ion mobility spectrometer (FAIMS), comprising: at least two focusing electrodes that are separated one from the other by a gap that decreases in width along a first direction; an electrode assembly disposed within the gap between the at least two focusing electrodes, the electrode assembly comprising: a first electrode having an approximately flat first electrode surface; a second electrode having an approximately flat second electrode surface, the second electrode disposed in a spaced-apart facing relationship with the first electrode so as to define a space of approximately uniform thicknesses between the first electrode surface and the second electrode surface for supporting during use the transmission of ions through the electrode assembly along the first direction; and, an electrical contact on at least one of the first electrode and the second electrode, and on each one of the at least two focusing electrodes, for receiving electrical signals for establishing within the space between the first electrode surface and the second electrode surface electric field conditions for selectively transmitting ions therethrough and for directing the selectively transmitted ions in a direction away from one of the at least two focusing electrodes and toward a central portion of the space.

According to an aspect of the invention there is provided a method for separating ions, comprising: providing along a first direction ions including a plurality of different ionic species, the ions for introduction into a space between a first flat electrode surface and a second flat electrode surface, the space decreasing in width along the first direction; applying between the first flat electrode surface and the second flat electrode surface a predetermined combination of an asymmetric waveform potential and a direct current compensation potential for separating one ionic species from the plurality of ionic species; applying between at least two lateral focusing electrodes a direct current potential for directing the one ionic species toward a central portion of the space; and, detecting the one ionic species.

BRIEF DESCRIPTION OF THE DRAWINGS

Exemplary embodiments of the invention will now be described in conjunction with the following drawings, in which similar reference numerals designate similar items.

DETAILED DESCRIPTION OF EMBODIMENTS OF THE INSTANT INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the scope of the invention. Thus, the present invention is not intended to be limited to the embodiments disclosed, but is to be accorded the widest scope consistent with the principles and features disclosed herein.

Figure 1:
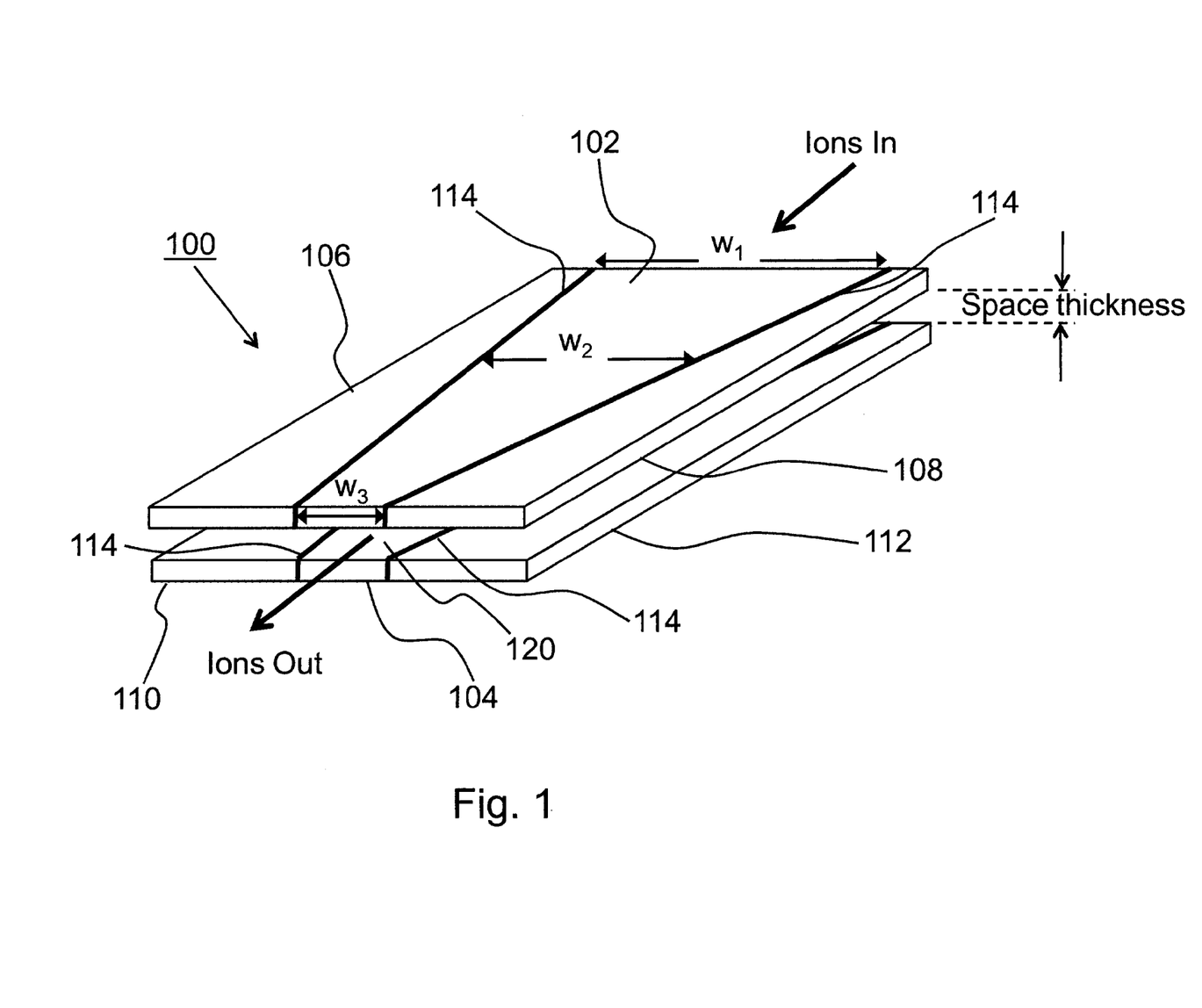
FIG. 1 is a simplified perspective view showing an electrode structure, for a FAIMS apparatus, according to an embodiment of the instant invention.

FIG. 1 is a simplified perspective view showing an electrode structure, for a FAIMS apparatus, according to an embodiment of the instant invention. The electrode structure, which is shown generally at 100, includes a central electrode assembly comprising a first electrode 102 and a second electrode 104. The first electrode 102 is spaced apart from the second electrode 104 so as to define a space 120, having an approximately uniform thickness, between an inwardly facing flat first electrode surface of the first electrode 102 and an inwardly facing flat second electrode surface of the second electrode 104. The space is for supporting during use the transmission of ions between an ion inlet end (Ions In) and an ion outlet end (Ions Out). For clarity, other conventional elements of the FAIMS apparatus, such as for instance an ionization source, curtain gas electrode assembly, ion inlet and ion outlet orifices, electrical controller, carrier gas supply system, detector system etc. have been omitted from FIG. 1.

The first electrode 102 and the second electrode 104 each have two non-parallel edges defining therebetween a width (w) that decreases along a length of the respective electrode. For instance, considering the first electrode 102, the width decreases from a maximum value $w_1$ at the ion inlet end, to an intermediate value $w_2$ part way along the length of the first electrode 102, to a minimum value $w_3$ at the ion outlet end. In the instant and non-limiting example, each one of the first electrode 102 and the second electrode 104 is in the shape of an isosceles trapezoid, and thus the width decreases continuously between the ion inlet end and the ion outlet end. Optionally, the width decreases in a discontinuous or stepwise manner. Further optionally, the width decreases at a non-constant rate between the ion inlet end and the ion outlet end.

Referring still to FIG. 1, a first focusing electrode 106 is disposed adjacent to one of the non-parallel edges of the first electrode 102 and a second focusing electrode 108 is disposed adjacent to the other one of the non-parallel edges of the first electrode 102. Similarly, a third focusing electrode 110 is disposed adjacent to one of the non-parallel edges of second electrode 104 and a fourth focusing electrode 112 is disposed adjacent to the other one of the non-parallel edges of the second electrode 104. The first focusing electrode 106 and the second focusing electrode 108 are isolated electrically from the first electrode 102 by an electrically insulating spacer material 114, such as for instance PEEK™, disposed therebetween. Similarly, the third focusing electrode 110 and the fourth focusing electrode 112 are isolated electrically from the second electrode 104 by an electrically insulating spacer material 114, such as for instance PEEK™, disposed therebetween. Optionally, the spacer material is omitted and the electrodes are separated one from another by an open gap.

The electrodes 102-112 are embedded in a not illustrated electrically insulating material, such as for instance PEEK™, and the entire electrode structure is supported within a housing including inlets and outlets for providing a flow of carrier gas through the space between the electrodes. Electrical contacts are provided on at least some of the electrodes 102-112 for coupling to a not illustrated electrical controller and for receiving various electrical signals therefrom. Optionally, a temperature controller is provided for controllably affecting the temperature of the gas between the electrodes 102-112, and/or for establishing during use a temperature gradient within the gas between the electrodes 102-112.

By the application of appropriate potentials to the flat-plate electrodes 102 and 104 using the not illustrated electrical controller, electric field conditions are established within the space 120 for separating ions according to the FAIMS principle. It should be noted that FAIMS is operable over a wide range of pressure values, from greater than atmospheric pressure down to the millitorr range. Ions are separated in FAIMS on the basis of the compound dependent behavior of $K_H$, the high field mobility constant, as a function of the applied electric field strength. It is to be understood that the strength of the field is actually E/N where E is the field in volts/cm and N is the number density of the bath gas. Clearly, the application of lower voltages is appropriate under conditions of lower gas pressure while higher voltages are required at higher gas pressure, in each case arriving at the same E/N value. The behavior of ions in the FAIMS device is based on changes in the mobility of the ion under conditions of changing E/N, which is often simplified to "conditions of changing electric field strength." Since an electric field gradient is not established along the direction of ion travel in FIG. 1, a carrier gas flow is used to transport the ions between the ion inlet end and the ion outlet end. Alternatively, at least some of the electrodes 102-112 are segmented along the length of the electrode structure, so as to support the application of different potentials to different segments for forming an electric field for accelerating ions along the direction of ion travel between the ion inlet end and the ion outlet end. Of course, operation of FAIMS down to millitorr pressure values necessitates the use of segmented electrodes since there is insufficient carrier gas pressure to transport the ions through the space 120.

Because the asymmetric waveform is applied between flat-plate electrodes 102 and 104, the ion separation resolution is very high in the device that is shown in FIG. 1. Additional potentials applied to the first through fourth focusing electrodes 106-112 prevent the ions from spreading out along the width and being lost from the device, and thus the ion transmission efficiency that is achievable using the electrode structure shown in FIG. 1 is higher than that of a flat plate FAIMS without the focusing electrodes. As is discussed in greater detail below, high DC potential is applied between facing ones of the first through fourth focusing electrodes 106-112, resulting in a lateral focusing field within a second space between the first and third focusing electrodes 106 and 110 and within a third space between the second and fourth electrodes 108 and 112.

Figure 2:
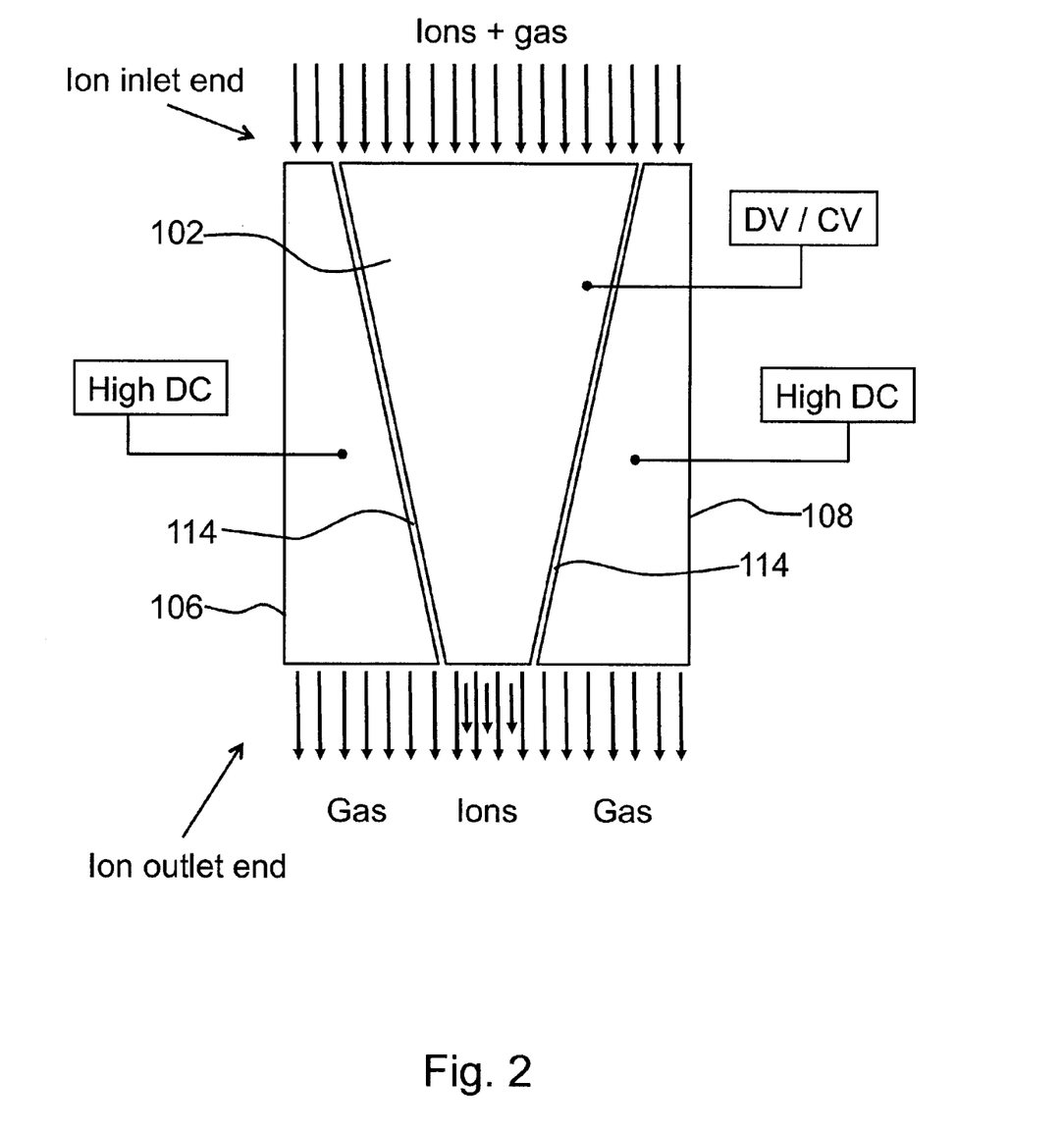
FIG. 2 is a simplified top-view of the electrode structure of FIG. 1, showing ion and gas flow therethrough.

Referring now to FIG. 2, a simplified top-view of the electrode structure of FIG. 1 is illustrated. In the specific and non-limiting example that is shown in FIG. 2, a predetermined combination of dispersion voltage (DV) and compensation voltage (CV) is applied to first electrode 102 via an electrical contact, and high DC potential is applied via electrical contacts on each of first focusing electrode 106 and second focusing electrode 108. The electrical contacts on the electrodes are coupled to one or more not illustrated electrical controllers, including a radio-frequency asymmetric waveform potential source and a direct current potential source.

Ions and gas are introduced into the ion inlet end of the space between the first electrode 102 and the second electrode 104. As the ions are carried along the length of the central electrode assembly, which comprises the first electrode 102 and the second electrode 104, the ions are directed laterally toward a central portion of the space 120, such that the ions emerge from the ion outlet end of the space as a relatively narrow band of ions. Since there are no barriers to the flow of the carrier gas between the various pairs of facing electrodes, the gas flows along a path between the ion inlet end and the ion outlet end across substantially the width of the electrode structure.

One consequence of the above-mentioned lateral focusing effect is that the ions enter into a relatively wide portion of the space 120 at the ion inlet end, permitting the ions to spread out to some extent when the ion density, and thus ion-ion repulsion forces, are at a maximum value. As the ions travel through the space 120, some of the ions suffer collisions with one of the electrode surfaces and are lost. Since the number of ions decreases between the ion inlet end and the ion outlet end, the ion density does not increase to an unacceptable value as the ions are focused increasingly toward the central portion of the space 120.

Figure 3:
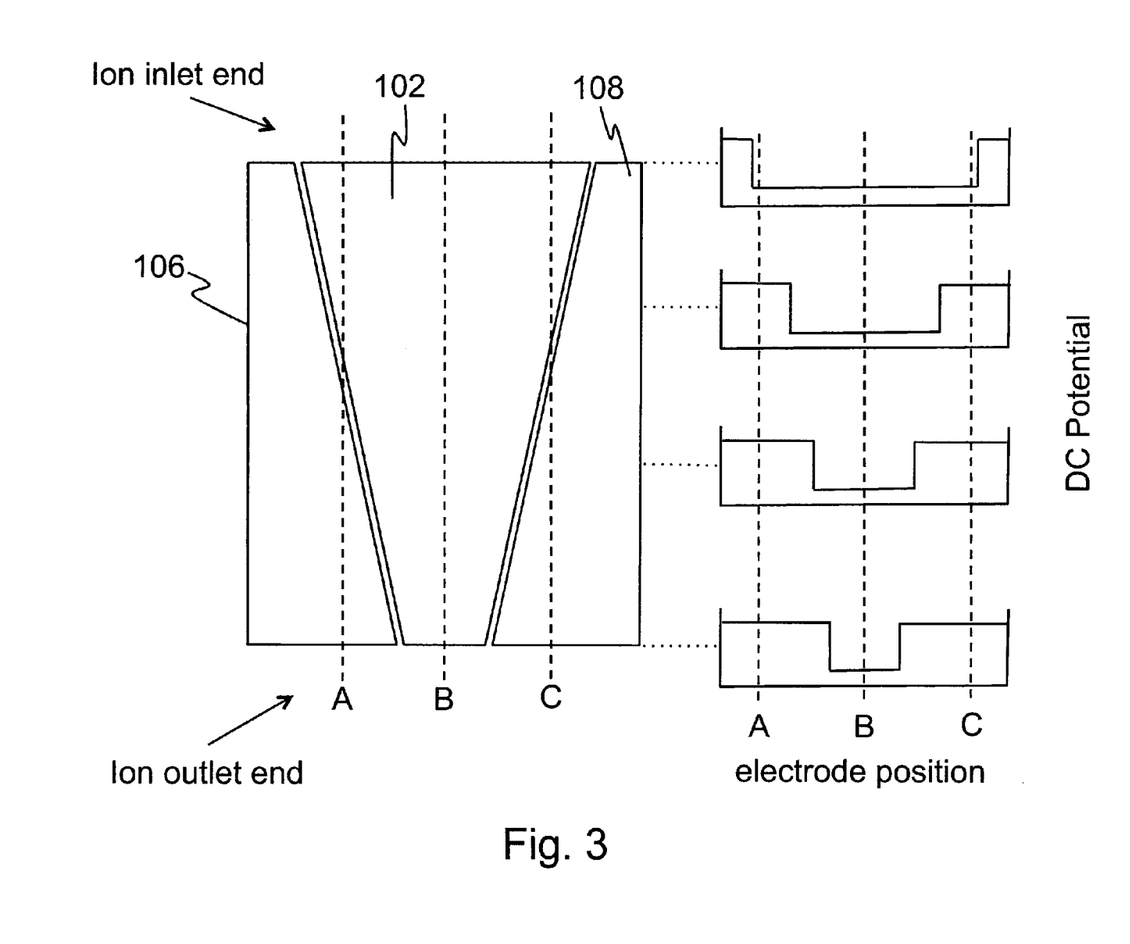
FIG. 3 illustrates the DC potential profile at different positions along the length of the electrode structure of FIG. 1.

FIG. 3 illustrates the DC potential profile at different positions along the length of the electrode structure of FIG. 1. The three dotted lines A, B and C extending along the length of the electrode structure between the ion inlet end and the ion outlet end are provided for reference, and correspond to the electrode positions A, B and C in the DC potential profile diagram. Near the ion inlet end (top of FIG. 3) the high DC potential is present only toward the edges of the electrode structure, and thus the ions occupy a relatively large volume of space immediately after being introduced into the space 120. The DC potential diagram shows that the high DC potential results in ions occupying a progressively smaller volume of space as they approach the ion outlet end. Accordingly, the high DC potential directs the ions that are flowing through the electrode structure toward the central portion of the space 120, proximate line B.

Figure 4:
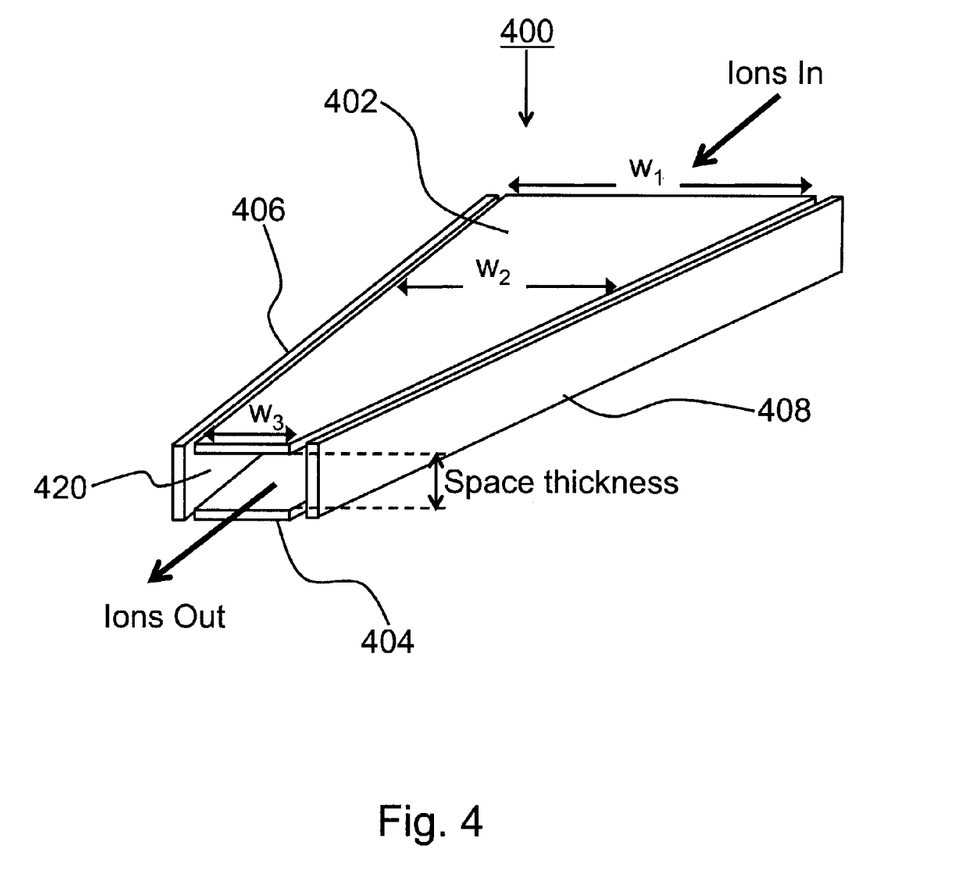
FIG. 4 is a simplified perspective view showing an electrode structure, for a FAIMS apparatus, according to an embodiment of the instant invention.

Referring now to FIG. 4, shown is a simplified perspective view of an electrode structure, for a FAIMS apparatus, according to an embodiment of the instant invention. The electrode structure, which is shown generally at 400, includes a central electrode assembly comprising a first electrode 402 and a second electrode 404. The first electrode 402 is spaced apart from the second electrode 404 so as to define a space 420, having an approximately uniform thickness, between an inwardly facing flat first electrode surface of the first electrode 402 and an inwardly facing flat second electrode surface of the second electrode 404. The space is for during use supporting the transmission of ions between an ion inlet end (Ions In) and an ion outlet end (Ions Out). For clarity, other conventional elements of the FAIMS apparatus, such as for instance an ionization source, curtain gas electrode assembly, ion inlet and ion outlet orifices, electrical controller, carrier gas supply system, detector system etc. have been omitted from FIG. 4.

The first electrode 402 and the second electrode 404 each have two non-parallel edges defining therebetween a width (w) that decreases along a length of the respective electrode. For instance, considering the first electrode 402 the width decreases from a maximum value $w_1$ at the ion inlet end, to an intermediate value $w_2$ part way along the length of the first electrode 402, to a minimum value $w_3$ at the ion outlet end. In the instant and non-limiting example, each one of the first electrode 402 and the second electrode 404 is in the shape of an isosceles trapezoid, and thus the width decreases continuously between the ion inlet end and the ion outlet end. Optionally, the width decreases in a discontinuous or stepwise manner. Further optionally, the width decreases at a non-constant rate between the ion inlet end and the ion outlet end.

Referring still to FIG. 4, a first focusing electrode 406 is disposed with a flat third electrode surface thereof adjacent to and facing the space 420, the electrode 406 being spaced an approximately constant distance from one of the non-parallel edges of each of the first electrode 402 and the second electrode 404. A second focusing electrode 408 is disposed with a flat fourth electrode surface thereof adjacent to and facing the space 420, the electrode 408 being spaced an approximately constant distance from the other one of the non-parallel edges of each of the first electrode 402 and the second electrode 404. The first focusing electrode 406 and the second focusing electrode 408 are disposed such that the third electrode surface and the fourth electrode surface are spaced apart from and facing one another. Moreover, each one of the first electrode surface and the second electrode surface is approximately orthogonal to each one of the third electrode surface and the fourth electrode surface. In FIG. 4 the first focusing electrode 406 and the second focusing electrode 408 are separated from the first electrode 402 and from the second electrode 404 by a gap. Optionally, the first focusing electrode 406 and the second focusing electrode 408 are isolated electrically from the first electrode 402 and the second electrode 404 by an electrically insulating spacer material (not shown), such as for instance PEEK™, disposed therebetween.

The electrodes 402-408 are embedded in a not illustrated electrically insulating material, such as for instance PEEK™, and the entire electrode structure is supported within a housing including inlets and outlets for providing a flow of carrier gas through the space between the electrodes. Electrical contacts are provided on at least some of the electrodes 402-408 for coupling to a not illustrated electrical controller and for receiving various potentials therefrom. Optionally, a temperature controller is provided for controllably affecting the temperature of the gas between the electrodes 402-408, and/or for establishing during use a temperature gradient within the gas between the electrodes 402-408.

By the application of appropriate voltages to the flat-plate electrodes 402 and 404 using the not illustrated electrical controller, electric field conditions are established within the space 420 for separating ions according to the FAIMS principle. It should be noted once again that FAIMS is operable over a wide range of pressure values, from greater than atmospheric pressure down to the millitorr range. Ions are separated in FAIMS on the basis of the compound dependent behavior of $K_H$, the high field mobility constant, as a function of the applied electric field strength. It is also to be understood that the strength of the field is actually E/N where E is the field in volts/cm and N is the number density of the bath gas. Clearly, the application of lower voltages is appropriate under conditions of lower gas pressure while higher voltages are required at higher gas pressure, in each case arriving at the same E/N value. The behavior of ions in the FAIMS device is based on changes in the mobility of the ion under conditions of changing E/N, which is often simplified to "conditions of changing electric field strength." Since an electric field gradient is not established along the direction of ion travel in FIG. 4, a carrier gas flow is used to transport the ions between the ion inlet end and the ion outlet end. Alternatively, at least some of the electrodes 402-408 are segmented along the length of the electrode structure, so as to support the application of different potentials to different segments for forming an electric field for accelerating ions along the direction of ion travel between the ion inlet end and the ion outlet end. Of course, operation of FAIMS down to millitorr pressure values necessitates the use of segmented electrodes since there is insufficient carrier gas pressure to transport the ions through the space 420.

Because the asymmetric waveform is applied between flat-plate electrodes 402 and 404, the ion separation resolution is very high in the device that is shown in FIG. 4. Additional potentials applied to the first and second focusing electrodes 406 and 408, respectively, prevent the ions from spreading out along the width and being lost from the device, and thus the ion transmission efficiency that is achievable using the electrode structure shown in FIG. 4 is higher than a flat plate FAIMS without the focusing electrodes. Application of high DC potential via contacts on the first focusing electrode 406 and the second focusing electrode 408 results in the creation of a lateral focusing field, which directs the ions toward a central portion of the space 420. One consequence of this lateral focusing effect is that the ions enter into a relatively wide portion of the space 420 at the ion inlet end, permitting the ions to spread out to some extent when the ion density, and thus ion-ion repulsion forces, are at a maximum value. As the ions travel through the space 420 some ions suffer collisions with one of the electrode surfaces and are lost. Since the number of ions decreases between the ion inlet end and the ion outlet end, the ion density does not increase to an unacceptable value as the ions are focused increasing toward the central portion of the space 420.

Figure 5:
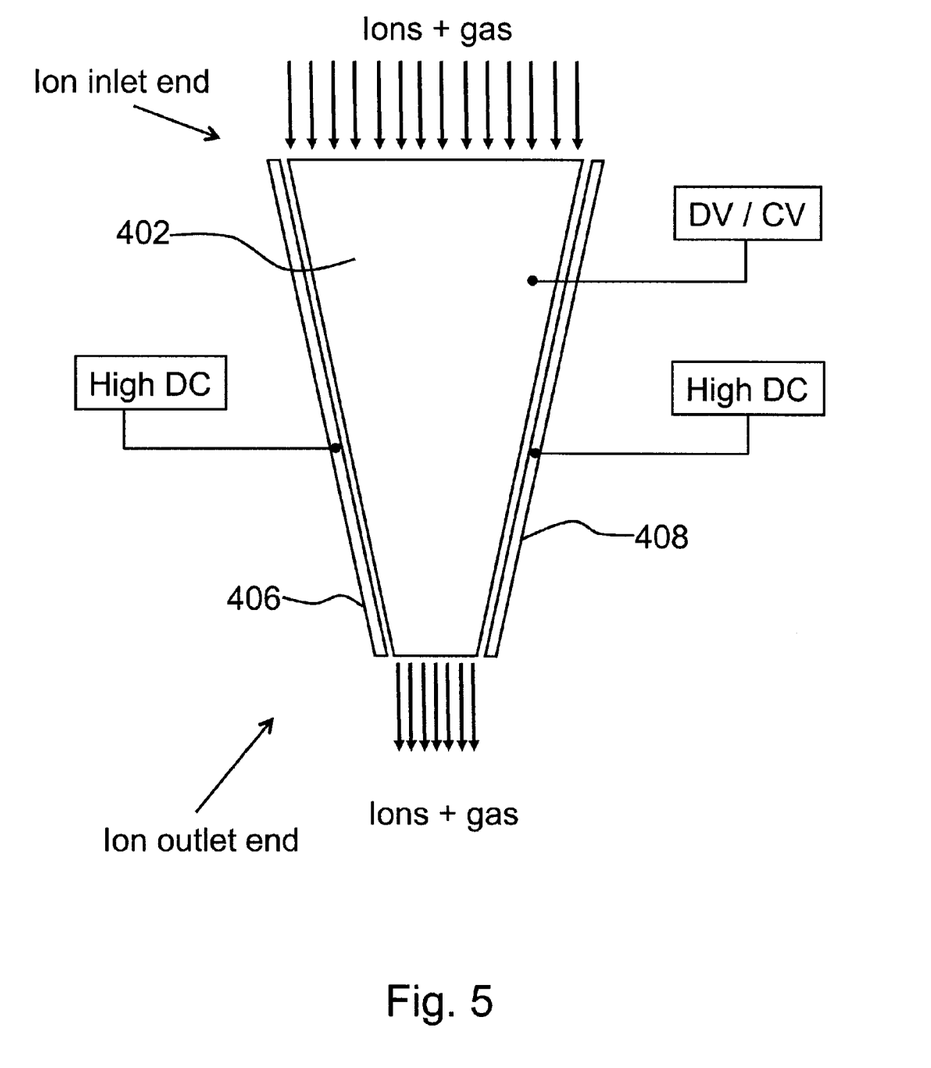
FIG. 5 is a simplified top-view of the electrode structure of FIG. 4.

Referring now to FIG. 5, a simplified top-view of the electrode structure of FIG. 4 is illustrated. In the specific and non-limiting example that is shown in FIG. 5, a predetermined combination of dispersion voltage (DV) and compensation voltage (CV) is applied to first electrode 402 via an electrical contact, and high DC potential is applied via electrical contacts on each of first focusing electrode 406 and second focusing electrode 408. The electrical contacts on the electrodes are coupled to one or more not illustrated electrical controllers, including a radio-frequency asymmetric waveform potential source and a direct current potential source.

Ions and gas are introduced into the ion inlet end of the space 420 between the first electrode 402 and the second electrode 404. As the ions are carried along the length of the central electrode assembly, which comprises the first electrode 402 and the second electrode 404, the ions are directed laterally toward a central portion of the space 420, thereby emerging from the ion outlet end of the space as a relatively narrow band of ions. In addition, the first focusing electrode 406 and the second focusing electrode 408 also form a physical barrier to the gas flow within the space, causing the gas to be "funneled" inwardly toward the center portion of space 420 in a direction toward the ion inlet end. However, when an electrically insulating material does not separate the electrodes 402, 404, 406 and 408, then some of the gas may flow out of the space 420 via the gaps between the various electrodes. Optionally, at least some of the electrodes 402, 404, 406 and 408 are adapted with slots or other apertures, or by making the electrodes porous, to enable gas, but not ions, to be pumped out of the interior region of the FAIMS cell along its length. For instance, slots or other apertures may be provided along at least a portion of the lengths of the electrodes 406 and 408, and optionally the electrode material that surrounds the slots or other apertures supports a mesh or other gas permeable structure, which may be electrically conductive so as to minimize electric field perturbations resulting from the presence of the slots or other apertures within the electrodes 406 and 408. Of course, the width, length and/or shape of the slots or apertures may be optimized for particular transport conditions, pressure being the major factor.

Figure 6:
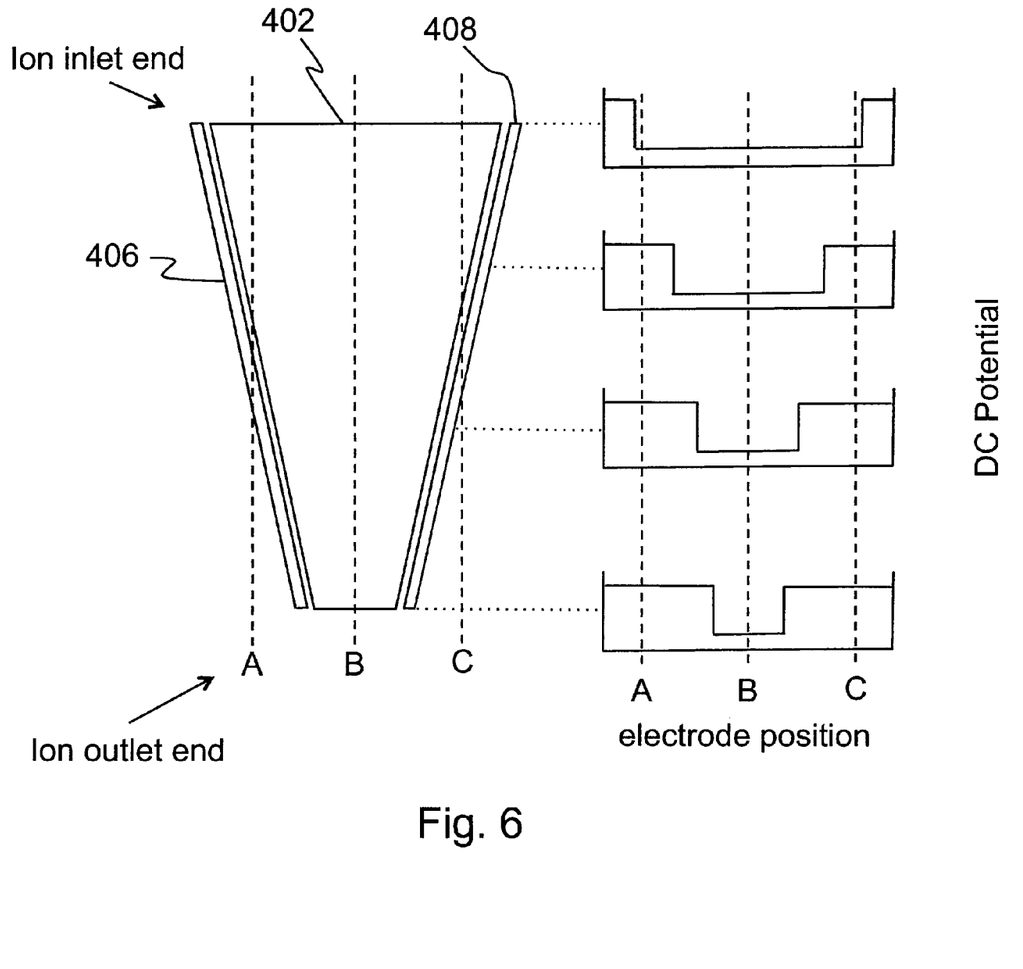
FIG. 6 illustrates the DC potential profile at different positions along the length of the electrode structure of FIG. 4.

FIG. 6 illustrates the DC potential profile at different positions along the length of the electrode structure of FIG. 4. The three dotted lines A, B and C extending along the length of the electrode structure between the ion inlet end and the ion outlet end are provided for reference, and correspond to the electrode positions A, B and C in the DC potential profile diagram. Near the ion inlet end (top of FIG. 6) the high DC potential is present only toward the edges of the electrode structure, and thus the ions occupy a relatively large volume of space immediately after being introduced into the space 420. The DC potential profile diagram shows that the high DC potential results in ions occupying a progressively smaller volume of space as they approach the ion outlet end. Accordingly, the high DC potential directs the ions that are flowing through the electrode structure toward the central portion of the space 420, proximate line B.

Figure 7A:
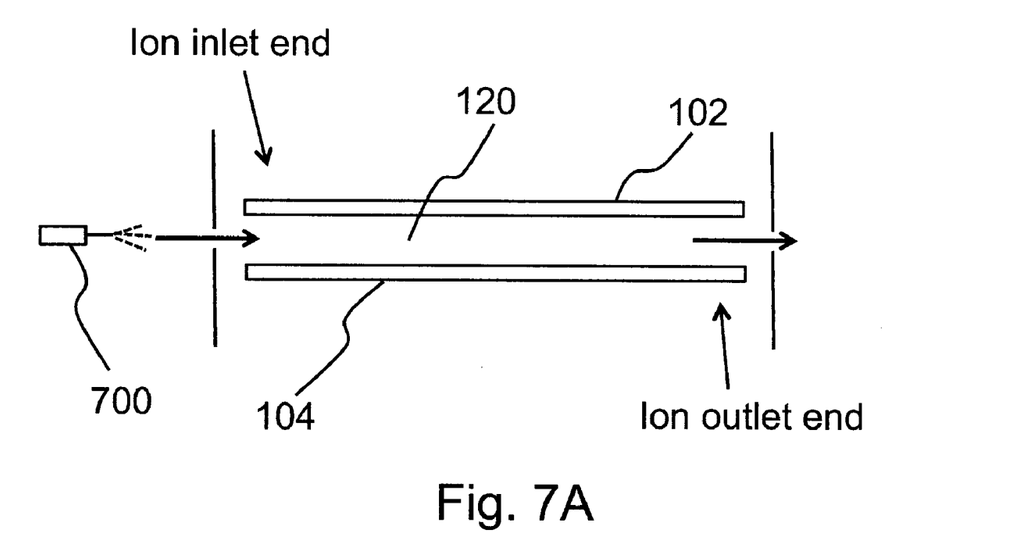
FIG. 7A shows in side cross-sectional view a first configuration of the ion inlet and ion outlet ends of an electrode structure according to an embodiment of the instant invention.

FIG. 7A shows in side cross-sectional view a first configuration of the ion inlet end and ion outlet end of an electrode structure, according to an embodiment of the instant invention. By way of a specific and non-limiting example the ions are produced at an ionization source 700, such as for instance an electrospray ionization (ESI) source, and are introduced via an orifice into the space 120 between the first electrode 102 and the second electrode 104. In particular, the ions are introduced along a direction that is parallel to the facing surfaces of the first and second electrodes. Some of the ions propagate through the space 120 to the ion outlet end, and are extracted through another orifice for one of detection and further analysis.

Figure 7B:
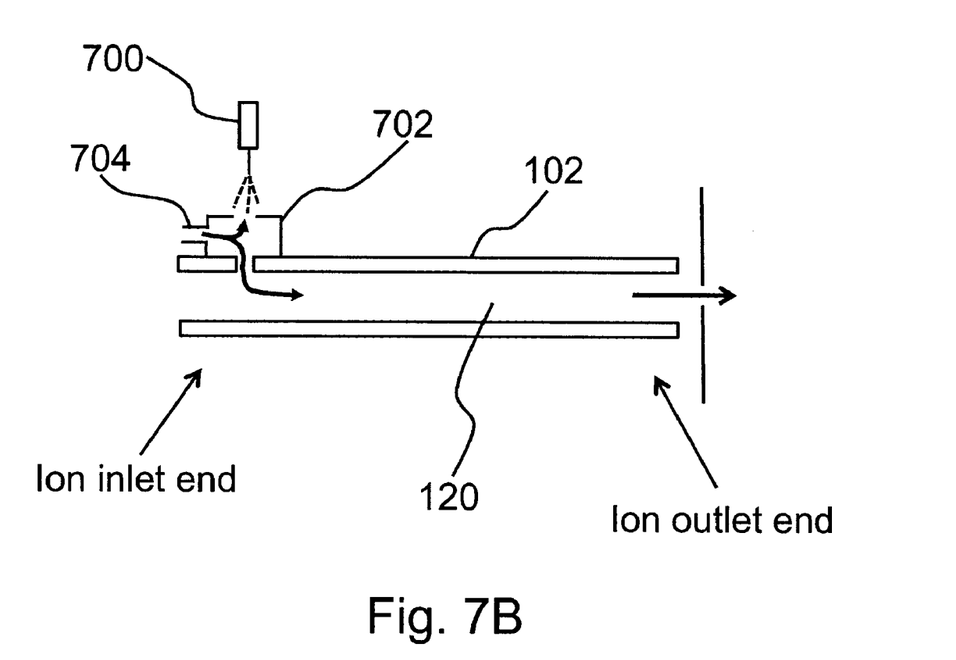
FIG. 7B shows in side cross-sectional view a second configuration of the ion inlet and ion outlet ends of an electrode structure according to an embodiment of the instant invention.

FIG. 7B shows in side cross-sectional view a second configuration of the ion inlet end and ion outlet end of an electrode structure according to an embodiment of the instant invention. By way of a specific and non-limiting example the ions are produced at an ionization source 700, such as for instance an ESI source, and are introduced via an orifice in a curtain gas electrode 702, where a flow of a carrier gas 704 assists in desolvating the ions and carrying the desolvated ions into the space 120 between the first electrode 102 and the second electrode 104. Some of the ions propagate through the space 120 to the ion outlet end, and are extracted through another orifice for one of detection and further analysis.

Of course, the ion inlet end and ion outlet end of the electrode structure that is shown in FIG. 4 optionally is configured according to either FIG. 7A or FIG. 7B. Optionally, another suitable ion inlet end configuration and/or another suitable ion outlet end configuration is used.

Figure 8A:
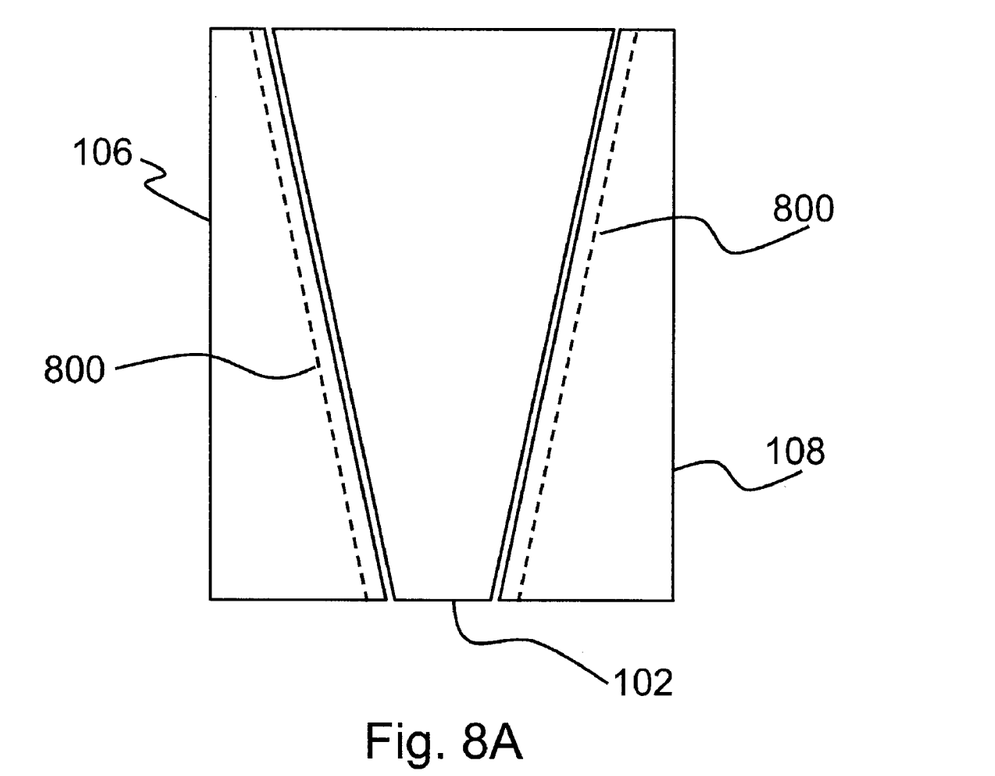
FIG. 8A is a top view of the electrode structure of FIG. 1 showing in phantom view the limits of optional, electrically insulating material disposed within the spaces between facing surfaces of the focusing electrodes; and, FIG. 8B is an end view of the ion outlet end of the electrode structure of FIG. 1 showing optional, electrically insulating material disposed within the spaces between facing surfaces of the focusing electrodes.
Figure 8B:
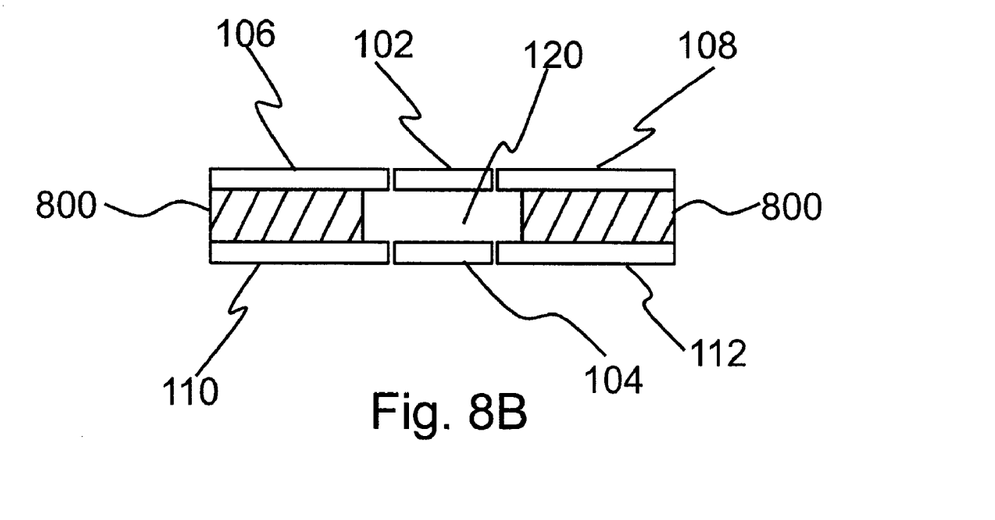

It is worth noting that in the specific and non-limiting example that is shown in FIG. 1, the space 120, the second space and the third space cooperate to define a continuous space between the various pairs of facing electrodes 102-112. Gas flows unimpeded through the continuous space between the ion inlet end and the ion outlet end, across the entire width of the electrode structure. Referring now to FIGS. 8A and 8B, shown is an optional variation of the electrode structure of FIG. 1. In particular, FIG. 8A is a top view of the electrode structure of FIG. 1 showing the limits (dashed lines) of optional, electrically insulating material 800 disposed within the spaces between facing surfaces of the focusing electrodes. The separation between the insulating material decreases between the ion inlet end and the ion outlet end, such that a flow of gas through the electrode assembly is directed generally inwardly toward a central portion of the space between first electrode 102 and second electrode 104 (not illustrated in FIG. 8a). Referring also to FIG. 8B, shown is an end view of the ion outlet end of the electrode structure of FIG. 1, in which optional, electrically insulating material 800 is disposed within the spaces between facing surfaces of the focusing electrodes. As is shown in FIG. 8b, the opening through which the gas exits from the space 120 at the outlet end is narrow compared to the overall width of the electrode structure. Directing the gas, with the ions entrained therein, toward the central portion of the space 120 further enhances ion transmission efficiency through the electrode structure.

Optionally, the focusing electrodes that are described with reference to FIGS. 1-8 also support alternate operating modes, such as for instance an rf-only mode. In the rf-only mode an alternating current (AC) rf waveform is applied to at least some of the focusing electrodes. When the electrodes are segmented along the length of the structure then optionally a first segmented portion of the electrode structure supports operation according to the FAIMS principle whilst another portion of the electrode structure supports operation in the rf-only mode.

The electrode structures that are shown in FIGS. 1-3 have an approximately rectangular overall shape, in which the outer edges of the focusing electrodes are approximately parallel and the ends of the electrode structure are at a right angle to both of the edges thereof. Of course, optionally the edges of the focusing electrodes are not parallel, similar to the structure that is shown in FIG. 4. Further optionally the ends of the electrode structure are shaped with concave or convex portions, or are at other than right angles with respect to the edges of the electrode structure. Furthermore, the various electrodes may be formed entirely of a conductive material, or may be electrode strips that are coated onto an electrically insulating material. Other suitable materials, such as for instance a conductive glass, optionally are used to form the electrodes. In addition, the electrodes are shown generally as thin, plate shaped electrodes with parallel flat surfaces on opposite sides thereof. Of course, the "back-sides" of the electrodes need not be flat or parallel to the "front-sides" of the electrodes, and the electrodes may be thicker or thinner than the proportions of the specific embodiments in the various figures would suggest.

Numerous other embodiments may be envisaged.

What is claimed is:

1. A high field asymmetric waveform ion mobility spectrometer (FAIMS), comprising:
   a first electrode having two non-parallel edges defining therebetween a width that decreases along a length of the first electrode, the first electrode having an approximately flat first electrode surface bounded by the two edges;
   a second electrode having two non-parallel edges defining therebetween a width that decreases along a length of the second electrode, the second electrode having an approximately flat second electrode surface bounded by the two edges, the second electrode disposed in a spaced-apart facing relationship with the first electrode so as to define an electrode assembly with a space of approximately uniform thicknesses between the first electrode surface and the second electrode surface, the two edges of the first electrode and the two edges of the second electrode cooperating to define two lateral boundaries of the electrode assembly with separation therebetween decreasing along a first direction, the space for supporting during use the transmission of ions through the electrode assembly along the first direction;
   at least two focusing electrodes including at least one focusing electrode disposed adjacent to each of the two lateral boundaries of the electrode assembly, the separation distance between the at least two focusing electrodes decreasing along the first direction;
   an electrical contact on at least one of the first electrode and the second electrode for receiving an asymmetric waveform potential and for applying a direct current compensation potential between the first electrode and the second electrode, for establishing an electric field within the space for separating ions according to the FAIMS principle; and,
   an electrical contact on each one of the at least two focusing electrodes for receiving a direct current electrical potential for directing ions in a direction away from one of the two lateral boundaries and toward a central portion of the space.

2. A high field asymmetric waveform ion mobility spectrometer according to claim 1, wherein the space between the first electrode surface and the second electrode surface has an ion inlet end and an ion outlet end, and wherein the width of the ion inlet end between the two lateral boundaries is greater than the width of the ion outlet end between the two lateral boundaries.

3. A high field asymmetric waveform ion mobility spectrometer according to claim 2, comprising an ion inlet and an ion outlet, wherein the ion inlet end is disposed closer to the ion inlet than to the ion outlet and the ion outlet end is disposed closer to the ion outlet than to the ion inlet, and wherein the separation between the two lateral boundaries of the electrode assembly decreases continuously between the ion inlet and the ion outlet.

4. A high field asymmetric waveform ion mobility spectrometer according to claim 2, wherein the at least two focusing electrodes include a first focusing electrode disposed adjacent to one of the two lateral boundaries of the electrode assembly and a second focusing electrode disposed adjacent to the other one of the two lateral boundaries of the electrode assembly, the first focusing electrode having a flat third electrode surface and the second focusing electrode having a flat fourth electrode surface, the third electrode surface disposed opposite and facing the fourth electrode surface with the space disposed therebetween.

5. A high field asymmetric waveform ion mobility spectrometer according to claim 4, wherein each one of the first electrode surface and the second electrode surface is orthogonal to each one of the third electrode surface and the fourth electrode surface.

6. A high field asymmetric waveform ion mobility spectrometer according to claim 4, wherein the first focusing electrode comprises a plurality of first focusing electrode segments, and wherein the second focusing electrode comprises a plurality of second focusing electrode segments, and wherein during use different electrical potentials are applied to corresponding pairs of first focusing electrode segments and second focusing electrode segments so as to produce an electric field gradient extending along the first direction between the ion inlet end and the ion outlet end of the space.

7. A high field asymmetric waveform ion mobility spectrometer according to claim 2, wherein the at least two focusing electrodes include a first focusing electrode and a second focusing electrode disposed one each adjacent to opposite ones of the two non-parallel edges of the first electrode, and a third focusing electrode and a fourth focusing electrode disposed one each adjacent to opposite ones of the two non-parallel edges of the second electrode.

8. A high field asymmetric waveform ion mobility spectrometer according to claim 7, wherein the first focusing electrode has a flat third electrode surface that is approximately co-planar with the first electrode surface, the second focusing electrode has a flat fourth electrode surface that is approximately co-planar with the first electrode surface, the third focusing electrode has a flat fifth electrode surface that is approximately co-planar with the second electrode surface, and the fourth focusing electrode has a flat sixth electrode surface that is approximately co-planar with the second electrode surface.

9. A high field asymmetric waveform ion mobility spectrometer according to claim 8, wherein the third electrode surface and the fifth electrode surface define a second space therebetween, the fourth electrode surface and the sixth electrode surface define a third space therebetween, and wherein the space, the second space and the third space cooperate to define a continuous space.

10. A high field asymmetric waveform ion mobility spectrometer according to claim 2, wherein the first electrode and the second electrode are each segmented along the respective lengths thereof for supporting operation in a FAIMS mode along a first portion of the respective lengths and for supporting operation in a radio-frequency only (rf-only) mode along a second portion of the respective lengths thereof.

11. A high field asymmetric waveform ion mobility spectrometer (FAIMS), comprising:
   at least two focusing electrodes that are separated one from the other by a gap that decreases in width along a first direction; and,
   an electrode assembly disposed within the gap between the at least two focusing electrodes, the electrode assembly comprising:
      a first electrode having a first side that is bounded by an isosceles trapezoid-shaped perimeter, the first side being approximately flat; and,
      a second electrode having a second side that is bounded by an approximately same isosceles trapezoid-shaped perimeter, the second side being approximately flat, the second electrode disposed in a spaced-apart facing relationship with the first electrode so as to define between the first side and the second side a space of approximately uniform thickness, the space for supporting during use the transmission of ions through the electrode assembly along the first direction;
wherein the decreasing width of the gap between the at least two focusing electrodes conforms approximately to the isosceles trapezoid-shaped perimeter of the first and second electrodes.

12. A high field asymmetric waveform ion mobility spectrometer according to claim 11, wherein the space between the first electrode surface and the second electrode surface has an ion inlet end and an ion outlet end, and wherein the width of the ion inlet end of the space is greater than the width of the ion outlet end of the space.

13. A high field asymmetric waveform ion mobility spectrometer according to claim 12, comprising an ion inlet and an ion outlet, wherein the ion inlet end is disposed closer to the ion inlet than to the ion outlet and the ion outlet end is disposed closer to the ion outlet than to the ion inlet, and wherein the width of the gap between the at least two focusing electrodes decreases continuously between the ion inlet and the ion outlet.

14. A high field asymmetric waveform ion mobility spectrometer according to claim 12, wherein the at least two focusing electrodes include a first focusing electrode and a second focusing electrode disposed one each on opposite sides of the space, such that a flat third electrode surface on the first focusing electrode is spaced apart from and facing a flat fourth electrode surface on the second focusing electrode, the space being bounded laterally by the third electrode surface and the fourth electrode surface.

15. A high field asymmetric waveform ion mobility spectrometer according to claim 14, wherein each one of the first electrode surface and the second electrode surface is orthogonal to each one of the third electrode surface and the fourth electrode surface.

16. A high field asymmetric waveform ion mobility spectrometer according to claim 14, wherein the first focusing electrode comprises a plurality of first focusing electrode segments, and wherein the second focusing electrode comprises a plurality of second focusing electrode segments, and wherein during use different electrical potentials are applied to corresponding pairs of first focusing electrode segments and second focusing electrode segments so as to produce an electric field gradient extending along the first direction between the ion inlet end and the ion outlet end of the space.

17. A high field asymmetric waveform ion mobility spectrometer according to claim 12, wherein the at least two focusing electrodes include a first focusing electrode and a second focusing electrode disposed one each adjacent to opposite edges of the first electrode, and a third focusing electrode and a fourth focusing electrode disposed one each adjacent to opposite edges of the second electrode.

18. A high field asymmetric waveform ion mobility spectrometer according to claim 17, wherein the first focusing electrode has a flat third electrode surface that is approximately co-planar with the first electrode surface, the second focusing electrode has a flat fourth electrode surface that is approximately co-planar with the first electrode surface, the third focusing electrode has a flat fifth electrode surface that is approximately co-planar with the second electrode surface, and the fourth focusing electrode has a flat sixth electrode surface that is approximately co-planar with the second electrode surface.

19. A high field asymmetric waveform ion mobility spectrometer according to claim 18, wherein the third electrode surface and the fifth electrode surface define a second space therebetween, the fourth electrode surface and the sixth electrode surface define a third space therebetween, and wherein the space, the second space and the third space cooperate to define a continuous space.

20. A high field asymmetric waveform ion mobility spectrometer (FAIMS), comprising:
at least two focusing electrodes that are separated one from the other by a gap that decreases in width along a first direction;
an electrode assembly disposed within the gap between the at least two focusing electrodes, the electrode assembly comprising:
a first electrode having an approximately flat first electrode surface;
a second electrode having an approximately flat second electrode surface, the second electrode disposed in a spaced-apart facing relationship with the first electrode so as to define a space of approximately uniform thicknesses between the first electrode surface and the second electrode surface for supporting during use the transmission of ions through the electrode assembly along the first direction; and,
an electrical contact on at least one of the first electrode and the second electrode, and on each one of the at least two focusing electrodes, for receiving electrical signals for establishing within the space between the first electrode surface and the second electrode surface electric field conditions for selectively transmitting ions therethrough and for directing the selectively transmitted ions in a direction away from one of the at least two focusing electrodes and toward a central portion of the space.

21. A high field asymmetric waveform ion mobility spectrometer according to claim 20, wherein at least an aperture is defined within at least one of the at least two focusing electrodes for allowing gas to flow outwardly from the space.

22. A method for separating ions, comprising:
providing along a first direction ions including a plurality of different ionic species, the ions for introduction into a space between a first flat electrode surface and a second flat electrode surface, the space decreasing in width along the first direction;
applying between the first flat electrode surface and the second flat electrode surface a predetermined combination of an asymmetric waveform potential and a direct current compensation potential for separating one ionic species from the plurality of ionic species;
applying between at least two lateral focusing electrodes a direct current potential for directing the one ionic species toward a central portion of the space; and,
detecting the one ionic species.

* * * * *